United States Patent
Crohn et al.

(10) Patent No.: US 8,388,340 B2
(45) Date of Patent: Mar. 5, 2013

(54) APICAL POSITION LOCATOR

(75) Inventors: Ilan Crohn, Nahariyha (IL); Jacob Levy, Haifa (IL)

(73) Assignee: Techdent Technologies Ltd., Nahariya (IL)

( * ) Notice: Subject to any disclaimer, the term of this patent is extended or adjusted under 35 U.S.C. 154(b) by 1070 days.

(21) Appl. No.: 12/094,278

(22) PCT Filed: Nov. 21, 2005

(86) PCT No.: PCT/IL2005/001228
§ 371 (c)(1),
(2), (4) Date: Oct. 29, 2008

(87) PCT Pub. No.: WO2007/057878
PCT Pub. Date: May 24, 2007

(65) Prior Publication Data
US 2009/0221931 A1 Sep. 3, 2009

(51) Int. Cl.
*A61C 19/04* (2006.01)
(52) U.S. Cl. ............................. 433/72; 33/513; 600/547
(58) Field of Classification Search .................. 600/547; 33/513; 433/224, 72
See application file for complete search history.

(56) References Cited

U.S. PATENT DOCUMENTS

| | | | |
|---|---|---|---|
| 3,753,434 A | 8/1973 | Pike et al. | |
| 3,901,216 A | 8/1975 | Felger | |
| 3,993,044 A | 11/1976 | McGuffin | |
| 4,243,388 A | 1/1981 | Arai | |
| 4,272,531 A | 6/1981 | DeMarinis | |
| 4,447,206 A | 5/1984 | Ushiyama | |
| 5,080,586 A * | 1/1992 | Kawai | 433/32 |
| 5,096,419 A * | 3/1992 | Kobayashi et al. | 433/72 |
| 5,112,224 A | 5/1992 | Shirota | |
| 5,211,556 A | 5/1993 | Kobayashi et al. | |
| 5,295,833 A | 3/1994 | Chihiro et al. | |
| 5,759,159 A * | 6/1998 | Masreliez | 600/547 |
| 6,221,031 B1 | 4/2001 | Heraud | |
| 6,968,229 B2 * | 11/2005 | Siemons | 600/547 |
| 2004/0101809 A1 * | 5/2004 | Weiss et al. | 433/224 |
| 2004/0225234 A1 * | 11/2004 | Siemons | 600/590 |
| 2006/0184061 A1 * | 8/2006 | Berger et al. | 600/554 |

* cited by examiner

*Primary Examiner* — Max Hindenburg
*Assistant Examiner* — Renee Danega

(57) ABSTRACT

A method and system are disclosed for detecting an apical position depending on the change in the impedance between a first electrode inserted into the root canal of the tooth of a patient and a second external electrode applied to a body surface of the patient. According to some embodiments, a regulated current such as an alternating current having a substantially constant amplitude is supplied between the two electrodes, and this current serves as a measurement signal. Alternatively or additionally, the frequency of the time varying (e.g. alternating) current is at least 50 KHZ, and/or at most about 300 KHZ. In some embodiments, the presently disclosed device includes a processing unit which determines a capacitance-governed function when the first electrode is in the apical region, and which determined a function at least moderately governed by resistance when the electrode is in the dental neck region. Optionally, the first electrode inserted into the root canal is a dental file or reamer.

26 Claims, 4 Drawing Sheets

APICAL POSITION LOCATOR

FIELD OF THE INVENTION

The present invention relates to dental treatment, and in particular to methods and apparatus for detecting an apical position in a root canal of a tooth.

BACKGROUND AND RELATED ART

During the course of dental treatment, dental files are inserted into the root canal to remove nerve and blood vessels. A major concern is to locate the apical constriction (minor foramen) for determining the working length and/or the apex (major foramen) to avoid surpassing the apex into the soft tissue.

Towards this end, a probe or electrode is typically inserted into the root canal, and the location of the apical region of the tooth is detected by measuring the resistance or the impedance between the inserted electrode and a second external electrode located outside of the tooth, usually connected to oral soft tissue. Thus, as the leading edge of the root canal probe or electrode approaches the apical position, the resistance or impedance between the root canal electrode and the external electrode changes. The resistance or impedance value is correlated with the depth of the probe tip in the root canal, allowing the dental practitioner to detect the apical position of the tooth. Typically, the apex locator instrument includes a display panel, which indicates the distance between a fixed point on the probe (e.g. the probe tip) and a fix point in the apical region (e.g. the apex, or a location of the apical constriction).

To date, apex locator instruments suffer from a number of shortcomings. For example, in many clinical situations, the value displayed by the apex instrument is not stable, making it difficult for the practitioner to determine the distance between the tip of the probe and the apex or apical constriction. Another source of inaccuracy stems from the fact that root canal dimensions and physical properties vary between specific teeth and patients, and thus many devices provide accurate readings for certain patients and erroneous readings for others.

Another source of inaccuracy stems from the fact that changes in an amplitude of current through biological tissue between the root canal and another location in the body may change the electrical properties of this biological tissue, introducing inaccuracies in a computed distance between the probe and the apical region.

Thus, there is an ongoing need for improved methods and apparatus for determining the position of a probe or electrode inserted within the root canal of a tooth.

Below is a listing of patents, published patent applications, and non-patent publications that provide potentially relevant related art. Each patent, published patent application, and non-patent publication is incorporated herein by reference in its entirety.

U.S. Pat. No. 4,272,531; U.S. Pat. No. 3,993,044; U.S. Pat. No. 4,447,206; U.S. Pat. No. 4,243,388; U.S. Pat. No. 3,901,216; U.S. Pat. No. 3,753,434; U.S. Pat. No. 5,096,419; U.S. Pat. No. 5,112,224; U.S. Pat. No. 5,211,556; U.S. Pat. No. 5,295,833 and U.S. Pat. No. 6,221,031.

SUMMARY OF THE INVENTION

The aforementioned needs are satisfied by several aspects of the present invention.

It is now disclosed for the first time apparatus for detecting an apical position depending on the change in the impedance between a first current supply electrode inserted into the root canal of a tooth of a patient and a second current supply electrode contacting a body surface of the patient. The presently disclosed apparatus includes (a) a detection apparatus including a measurement signal generator adapted to produce a regulated current (e.g. an alternating current) between the first and second current supply electrodes, the detection apparatus adapted to sense an impedance parameter between the first and second electrodes (for example, by detecting a voltage parameter that is a known function of the voltage between the first and second current supply electrodes), and (b) a processing unit for deriving from the sensed parameter a multiple of a distance between a fixed point on the first current supply electrode and the apical position of the tooth.

According to some embodiments, the regulated current has a substantially constant current amplitude, e.g. a current whose amplitude is substantially independent of a value of the distance between the fixed point on the first current supply electrode and the apical position.

According to some embodiments, the regulated current is a time varying current (e.g. an alternating current). Time varying regulated currents of any frequency are within the scope of the present invention. According to some embodiments, the current has a frequency of at least 50 KHz. In some embodiments, the current is a "medium frequency" current, having a frequency of at least 50 KHz and at most 300 KH, at most 250 KHZ, or at most 200 KHZ.

It is noted that, according to some embodiments, during the course of deriving the multiple of the distance, the processing unit determines a capacitance-governed function when the first electrode (e.g. the fixed point of the electrode) is in the apical region, and the processing unit determines a function at least moderately governed by resistance when the first electrode is in a dental neck region.

According to some embodiments, the presently disclosed device further includes a display unit for displaying output received from the processing unit.

It is now disclosed for the first time apparatus for detecting an apical position depending on the change in the impedance between a first current supply electrodes inserted into the root canal of a tooth of a patient and a second current supply electrode contacting a body surface of the patient. The presently disclosed apparatus includes (a) a detection apparatus including a measurement signal generator adapted to produce between the first and second current supply electrodes a voltage (e.g. an alternating current voltage) whose amplitude depends on a position of the first current supply electrode within the root canal of the tooth, the detection apparatus adapted to sense a impedance parameter between the first and second current supply electrodes and/or a parameter related to a voltage between the first and second current supply electrodes, and (b) a processing unit for deriving from the sensed parameter a multiple of a distance between a fixed point on the first current supply electrode and the apical position of the tooth.

According to some embodiments, a voltage whose amplitude "substantially" depends on a position of the first current supply electrode within the root canal of the tooth, e.g. whose amplitude changes by at least 10%, or by at least 30% as the position of the first current supply electrode within the root canal changes. In one example, the amplitude of the voltage changes by at least 10%, or by at least 30% when the fixed point of the first electrode moves between a dental neck region of the root canal and an apical region.

It is now disclosed for the first time a device comprising (a) a dental file electrode insertable into the root canal of a tooth of a patient, (b) an external electrode adapted to contact a body surface of the patient, and (c) a detection apparatus including a measurement signal generator adapted to produce a regulated current (e.g. an alternating current) between the dental file and external electrodes, the detection apparatus adapted to sense an impedance related parameter to generate an output signal indicative of a distance between a fixed point on the dental file electrode and the apical position of the tooth.

It is now disclosed for the first time a device comprising (a) a dental file electrode insertable into the root canal of a tooth of a patient, (b) an external electrode adapted to contact a body surface of the patient and (c) a detection apparatus including a measurement signal generator adapted to produce between the dental file and external electrodes a voltage whose amplitude depends on a position of the dental file electrode within the root canal of the tooth (e.g. a voltage of an alternating current), the detection apparatus adapted to sense an impedance related parameter between the first and second current supply electrodes (for example, by detecting a voltage parameter that is a known function of the voltage between the first and second current supply electrodes) 4 to generate an output signal indicative of a distance between a fixed point on the first electrode and the apical position of the tooth.

According to some embodiments, the presently disclosed device further includes (d) a processing unit for deriving from the output signal a multiple of a distance between the fixed point on the first electrode and the apical position of the tooth.

It is now disclosed for the first time apparatus for detecting an apical position depending on the change in the impedance between a first electrode inserted into the root canal of a tooth of a patient and a second electrode contacting a body surface of the patient. The presently disclosed apparatus includes (a) a detection apparatus including a measurement signal generator adapted to produce electrical signals (e.g. electrical signals of an alternating current) having a frequency of at least 50 KHZ and at most 200 KHZ (or at most 250 KHZ, or at most 250 KHZ) between the first and second power supply a measurement signal, the detection apparatus adapted to sense an impedance related parameter (e.g. an impedance related parameter between the first and second electrodes) and (b) a processing unit for deriving from the sensed parameter a multiple of a distance between a fixed point on the first electrode and the apical position of the tooth.

It is now disclosed for the first time a device comprising a dental file electrode insertable into the root canal of a tooth of a patient, an external electrode adapted to contact a body surface of the patient and a detection apparatus including a measurement signal generator adapted to produce between the dental file and external electrodes electrical signals having a frequency of at least 50 KHZ and at most 200 KHZ, the detection apparatus adapted to sense an impedance related parameter (e.g. an impedance related parameter between the dental file and external electrodes) to generate an output signal indicative of a distance between a fixed point on the first electrode and the apical position of the tooth.

It is now disclosed for the first time a device comprising (a) a dental file electrode insertable into the root canal of a tooth, at least a portion of an elongate surface of the dental file electrode being uninsulated, (b) an external electrode adapted to contact a body surface, and (c) a detection apparatus including a measurement signal generator adapted to produce between the dental file and external electrodes electrical signals having a frequency of at least 50 KHZ, the detection apparatus adapted to sense an impedance related parameter (e.g. an impedance related parameter between the dental file and external electrode) to generate an output signal indicative of a distance between a fixed point on the first electrode and the apical position of the tooth.

As used herein, an "elongate surface" of an elongate body is the surface perpendicular to the elongate axis substantially not near each end of the elongate body. In one embodiment, the distance between points of the "elongate surface" and an end of the elongate body is at least 0.1 times the length of the elongate body. In some embodiments, the distance between points of the "elongate surface" and an end of the elongate body is at least 0.2 times the length of the elongate body.

It is now disclosed for the first time a device comprising (a) a first electrode insertable into the root canal of a tooth of a patient, (b) a second electrode adapted to contact a body surface of the patient and (c) a detection apparatus including a measurement signal generator adapted to produce between the first and second electrodes electrical signals having a frequency of at least 50 KHZ, the detection apparatus adapted to sense an impedance related parameter (e.g. an impedance related parameter between the first and second electrodes) to generate an output signal indicative of a distance between a fixed point on the first electrode and the apical position of the tooth, the measurement signal generator adapted to supply a maximum of 40 microamperes between the first and second electrodes.

It is now disclosed for the first time apparatus for detecting an apical position depending on the change in the impedance between a first electrode inserted into the root canal of a tooth of a patient and a second electrode contacting a body surface of the patient. The presently disclosed apparatus comprises (a) a detection apparatus including a measurement signal generator adapted to produce a measurement signal (e.g. alternating current) between the first and second electrodes, the detection apparatus adapted to sense an impedance-related parameter (e.g. by sensing a voltage parameter) between the first and second current supply electrodes, and (b) a processing unit for deriving from the sensed parameter a multiple of a distance between a fixed point on the first electrode and the apical position of the tooth, wherein the processing unit determines a capacitance-governed function when the first electrode is in the apical region, and the processing unit determines a function at least moderately governed by resistance when the electrode is in a dental neck region.

It is now disclosed for the first time a method of measuring penetration in a root canal of a tooth of a patient. The presently disclosed method includes (a) inserting a first electrode into the root canal of a tooth, (b) applying a second electrode to a body surface of the patient, (c) supplying a regulated current between the first and second electrodes, and (d) determining (e.g. measuring) an impedance parameter between the first and second electrodes, the impedance parameter indicative of a distance between a fixed point on the first electrode and an apical position of the tooth.

According to some embodiments, the second electrode is applied to the position within the oral cavity of the patient.

Alternatively or additionally, the second electrode is applied to the position outside of the oral cavity of the patient.

According to some embodiments, the first electrode is inserted to a plurality of depths within the root canal, and an amplitude of the regulated current is substantially independent of the distance between the fixed point and the apical position.

It is noted that each "depth" is characterized by a different distance between a fixed point on the first electrode (e.g. the electrode being inserted into the root canal) and the apical position of the tooth.

According to some embodiments, the regulated current is a substantially low amplitude regulated current which never exceeds 40 microamperes when the first electrode is near an apical region.

According to some embodiments, the regulated current is a time varying current, and a frequency of the time varying current is at most 250 KHZ, or at most 300 KHZ, or at most 200 KHZ.

According to some embodiments, the regulated current is a time varying current, and a frequency of the time varying current is at least 25 KHZ, or at least 50 KHZ.

According to some embodiments, the time varying current is has a frequency between 50 KHZ and 200 KHZ, or between 50 KHZ and 250 KHZ, or between 50 KHZ and 300 KHZ.

According to some embodiments, the determining includes determining a capacitance-determined impedance parameter when the fixed point is in an apical region of the root canal, and determining an impedance parameter whose value is at least moderately governed by resistance when the fixed point is in a dental neck region of the root canal.

According to some embodiments, the first electrode is a dental file.

According to some embodiments, at least a portion of an elongate surface of the first electrode is uninsulated.

According to some embodiments, the presently disclosed method further includes the step of deriving from the determined impedance parameter a multiple of a distance between the fixed point on the electrode and the apical position of the tooth.

According to some embodiments, the deriving includes deriving a capacitance-governed function when the fixed point is in an apical region of the root canal, and deriving a function at least moderately governed by resistance when the fixed point is in a dental neck region of the root canal.

It is now disclosed for the first time a method of measuring penetration in a root canal of a tooth of a patient. The presently disclosed method includes inserting a first electrode into a root canal of a tooth, (b) applying a second electrode to a body surface of the patient, (c) supplying a measurement signal between the first and second electrodes and (d) determining (e.g. measuring) an impedance parameter between the first and second electrodes, the impedance parameter indicative of a distance between a fixed point on the first electrode and an apical position of the tooth, wherein the first electrode is inserted to a plurality of distinct depths within the root canal, and for each the depth, an amplitude voltage of the measurement signals depends, or substantially depends, on the distance between the fixed point and the apical position.

It is now disclosed for the first time a method of measuring penetration in a root canal of a tooth of a patient. The presently disclosed method includes (a) inserting a first electrode into a root canal of a tooth, (b) applying a second electrode to a body surface of the patient, (c) supplying an electrical measurement signal (e.g. alternating current) having a frequency of at least 50 KHZ between the first and second electrodes, and (d) determining (e.g. measuring) an impedance parameter between the first and second electrodes, the impedance parameter indicative of a distance between a fixed point on the first electrode and an apical position of the tooth.

According to some embodiments, at least a portion of an elongate surface of the first electrode is uninsulated.

It is now disclosed for the first time a method of measuring penetration in a root canal of a tooth of a patient. The presently disclosed method includes (a) inserting a first electrode into the root canal of a tooth, applying a second electrode to a body surface of the patient; (c) supplying a regulated current between the first and second electrodes, and (d) determining (e.g. measuring) an impedance parameter between the first and second electrodes, the impedance parameter indicative of a distance between a fixed point on the first electrode and an apical position of the tooth, wherein the determining includes determining a capacitance-determined impedance parameter when the fixed point is in an apical region of the root canal, and determining an impedance parameter whose value is at least moderately governed by resistance when the fixed point is in a dental neck region of the root canal.

It is now disclosed for the first time a method of measuring penetration in a root canal of a tooth of a patient. The presently disclosed method includes (a) inserting a first electrode into the root canal of the tooth, (b) applying a second electrode to a body surface of the patient, (c) supplying a regulated current between the first and second electrodes, and (d) determining (e.g. measuring) an impedance parameter between the first and second electrodes, and (e) deriving from the determined impedance parameter a multiple of a distance between a fixed point on the first electrode and the apical position of the tooth.

These and further embodiments will be apparent from the detailed description and examples that follow.

DETAILED DESCRIPTION OF AN EXEMPLARY EMBODIMENT

The present invention will now be described in terms of specific, example embodiments. It is to be understood that the invention is not limited to the example embodiments disclosed. It should also be understood that not every feature of methods and devices for detecting an apical position are necessary to implement the invention as claimed in any particular one of the appended claims. Various elements and features of devices are described to fully enable the invention. It should also be understood that throughout this disclosure, where a process or method is shown or described, the steps of the method may be performed in any order or simultaneously, unless it is clear from the context that one step depends on another being performed first.

Figure 1A:
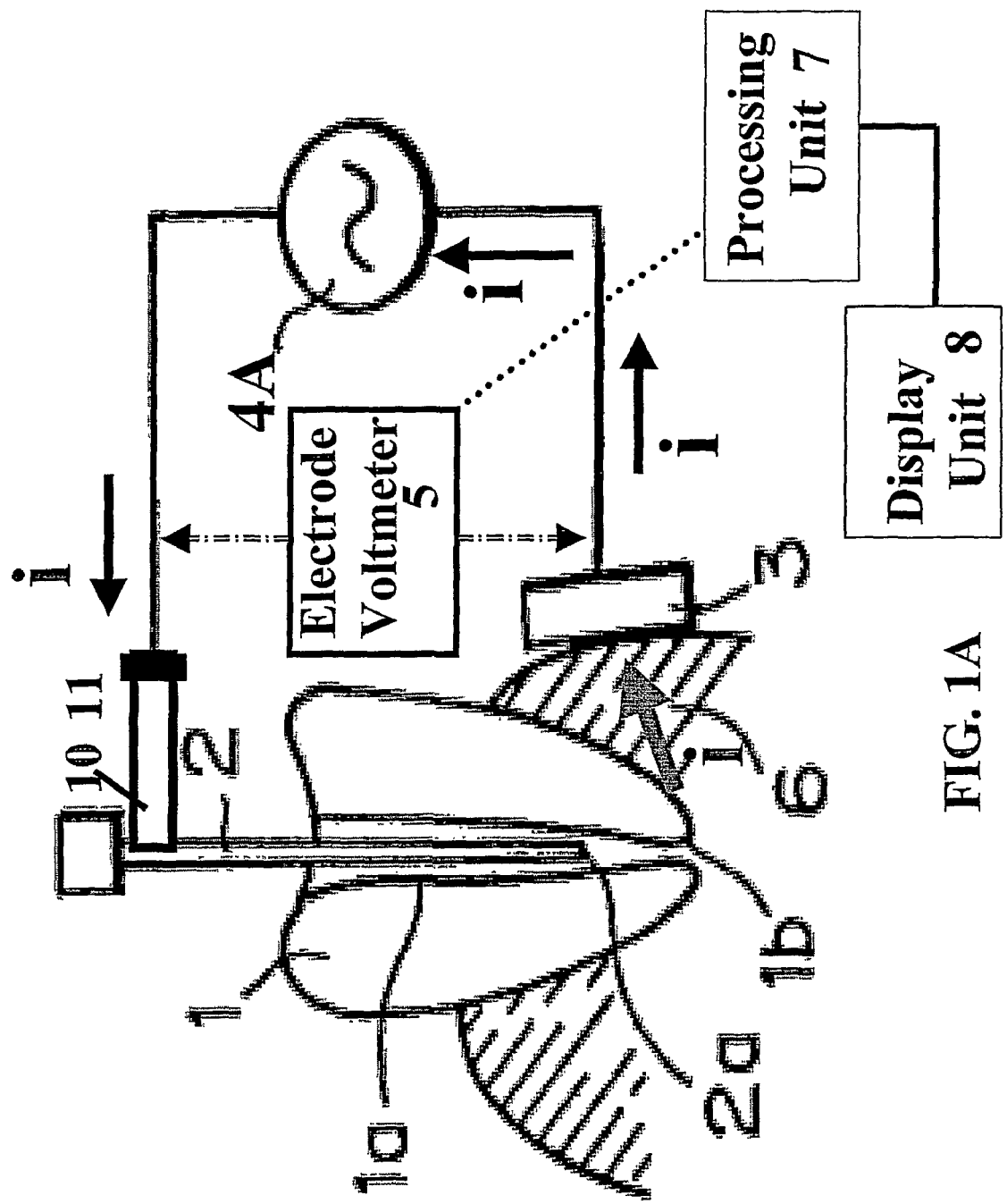
FIGS. 1-3 provide diagrams of exemplary systems for detecting an apical position according to some embodiments of the present invention.

FIG. 1 provides a diagram of an exemplary device for detecting an apical position of a tooth 1 according to some embodiments of the present invention. Thus, as illustrated in FIG. 1, the tooth has a root canal with a dental neck region 1a and an apical section 1b. A root canal electrode 2 is inserted into the root canal 1a, and the display unit 8 of the device provides output indicative of a distance between a fixed point on the electrode 2 (e.g. the tip of the electrode 2a) and a fixed point within the apical section 1b. As shown in FIG. 1, a regulated current, for example an alternating current having a substantially fixed amplitude, flows between the root canal electrode and the external electrode 3, which contacts a surface of the patient's body.

In some embodiments, the position of the root canal electrode 2 may be determined by a processing unit 7 in accordance with electrical measurements for example, output generated by a voltmeter 5 between two locations in the measurement circuit as will be explained below.

Experiments performed by the present inventors have shown that use of a regulated current source (e.g. a regulated alternating current source), and in particular, a current source having a substantially constant amplitude, is useful for producing stable measurements of the position of the root canal electrode 2 within the root canal.

Not wishing to be bound by any particular theory, it is believed that use of a constant voltage source with un-regulated fluctuating current (e.g. current whose amplitude fluctuates as the root canal electrode is inserted deeper into the root canal, or raised in the canal) may influence the electrical properties of the biological tissue associated with the root canal and the apex (for example, tissue in the canal and/or below the apex). Because the determined apical position depends on the measured electrical properties of the biological tissue, it is believed that use of a constant voltage source with un-regulated fluctuating current can therefore, in certain situations, introduce instabilities and inaccuracies in the assessed distance between the root canal electrode 2 and the apex (or apical constriction) of the tooth. Once more, not wishing to be bound by any particular theory, it is thus believed that, in contrast, regulated current sources, and in particular a current sources having a substantially constant amplitude, are useful for reducing these inaccuracies and instabilities certain clinically relevant situations.

As used herein, production of "a regulated current" entails producing a current with a predefined current profile. Examples of producing a "regulated current" include producing a constant amplitude current and a substantially constant amplitude current.

The terms "apical section" or "apical region" relate to the region between the apical constriction (minor foramen) (or points less than 0.2 mm above the apical constriction) and the apex (major foramen) of the tooth. It is noted the term "apical position" is intended in the broadest sense, and includes any point in the apical region. In some embodiments, the "apical position" is specifically intended to mean the apex (major foramen) of the tooth.

The term "dental neck" region is the region of the root canal above the apical section, e.g. above the apical constriction, or above a point between 0 and 0.2 mm above the apical constriction.

According to some embodiments, a "regulated current source 4A having a substantially constant current amplitude" supplies, between the root canal electrode 2 and the external electrode 3, current whose amplitude is constant within a tolerance of no more than 10%. According to some embodiments, the amplitude is constant within a tolerance of no more than 5%. According to some embodiments, the amplitude is constant within a tolerance of no more than 1%.

As used herein, an "impedance related parameter" is a parameter that is a known function of an impedance. One example of an "impedance related parameter" is an impedance.

There is no limitation on the amplitude or amount of current which flows between the root canal electrode and the external electrode. In exemplary embodiments, between 1 microampere and 120 microamperes flow between the two electrodes. In some embodiments, between 5 microampere and 55 microamperes flow between the two electrodes. In one particular example, between 8 and 12 microampere flow between the two electrodes.

According to exemplary embodiments of FIG. 1, the regulated or substantially constant amplitude current is supplied by a current supply device or measurement signal generator 4A adapted to send a current i through the optional wire terminal 11, the root canal electrode 2, and the region between the tip 2A of the root canal electrode and the external electrode 3. In the example of FIG. 1, the wire terminal 11 is the end of a flexible cable (e.g. about 5 ft long), and is connected to the root canal electrode 2 with a spring clip 10. In the example of FIG. 1, the external electrode 3 is an oral electrode connected to the gingival 6, though this is not a limitation of the present invention, and in various embodiments, the external electrode 3 may contact or be "applied to" any "body surface" of the patient. In one example of applying an electrode a "body surface" or contacting a "body surface," the external electrode 3 contacts actual tissue of the patient outside of the tooth. The term "body surface" includes, for example, any tissue of the patient, including tissue inside the patient's mouth and outside of the patient's mouth, including, for soft tissue. In one example, the "body surface" is a patient's lip, or cheek. In one example, the "body, surface" is the patient's hands or feet. The term "applying an electrode" to a body surface includes actually contacting the body surface, and/or contacting a conducting object or a partially conducting object through which current flows to the body surface of the patient.

Figure 1B:
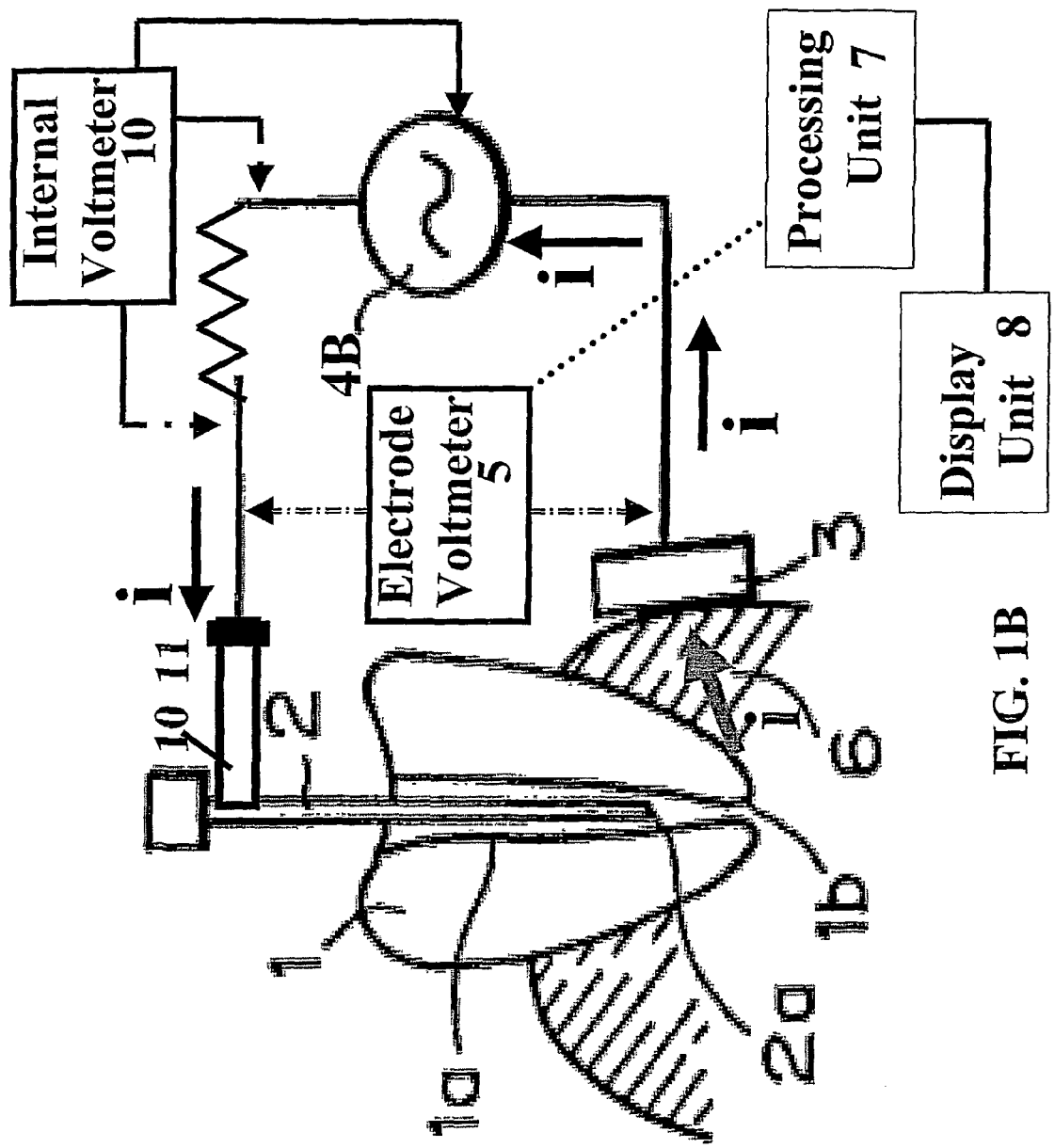

It is noted that constant amplitude current sources 4A are well known in the art, and are either available off the shelf, or can be configured in any number of ways. FIG. 1B provides an exemplary configuration where the amplitude of a constant voltage source 4B is adjusted in accordance with a reading from an internal voltmeter 10 on the circuit such that the current i remains substantially constant. Nevertheless, it is stressed that this is merely an illustrative example and is not intended as limiting. Any constant amplitude current source using any mechanism for maintaining a substantially amplitude current is within the scope of the present invention.

According to some embodiments, in one example, measurement output (e.g. output from a voltmeter 5) of an impedance parameter (e.g. a parameter that is a function of the impedance at a given frequency) between the root canal electrode 2 and the external electrode is determined. The measured impedance parameter (for example, derived by using the voltmeter 5 to measure an instantaneous voltage amplitude between the root canal electrode 2 and the external electrode 3) is correlated with the depth of the root canal electrode tip in the root canal, allowing the arrival of the tip at the root apex to be detected. Thus, in some embodiments, the device includes a processing unit 7 which is operative to output a distance (or a multiple of a distance) between a fixed point of the root canal electrode 2 (e.g. the tip of the electrode) and a fixed point in the apical section 1B (e.g. the root apex, the location of the apical constriction, or any other fixed point). In one example, the processing unit includes a look up table correlating the instantaneous voltage amplitude measured by the voltmeter 5, with the distance between a fixed point of the root canal electrode 2 (e.g. the tip of the electrode) and a fixed point in the apical section.

In the specific example depicted in FIG. 1, both the root canal electrode 2 and the external electrodes 3 are "current supply electrodes"—e.g. electrodes which supply the regulated current from the current supply device or measurement signal generator 4A through the biological tissue between the electrodes. Furthermore, it is noted that in the example of FIG. 1, the electric potential between the electrodes are measured, more example by electrode voltmeter 5, and thus the electrodes (2 and 3) may also be considered "measurement electrodes." It is noted that the actual voltage between the measurement electrodes need not be measured directly—in some embodiments, another parameter (e.g. electrical potential difference) indicative of the actual voltage between measurement electrode 2 and 3 (or the impedance between the measurement electrode 2 and 3) is measured. Thus, according to the example of FIG. 1, the current supply electrodes also function as measurement electrodes.

It is noted that optionally, a portion of the root canal, or the entirety of the root canal is filled with a liquid (e.g. saline, blood) and/or tissue (e.g. blood vessels, nerves, pulp) while the electrode 2 is inserted into the root canal.

In some embodiments, the root canal electrode or probe 2 is a dental file or reamer inserted into the root canal. Nevertheless, this is not a limitation of the present invention, and any electrode or probe appropriately dimensioned for insertion into the root canal 2 is appropriate for the present invention.

The terms "dental file" and "reamers" relate to tools used for root canal treatment.

Figure 2:
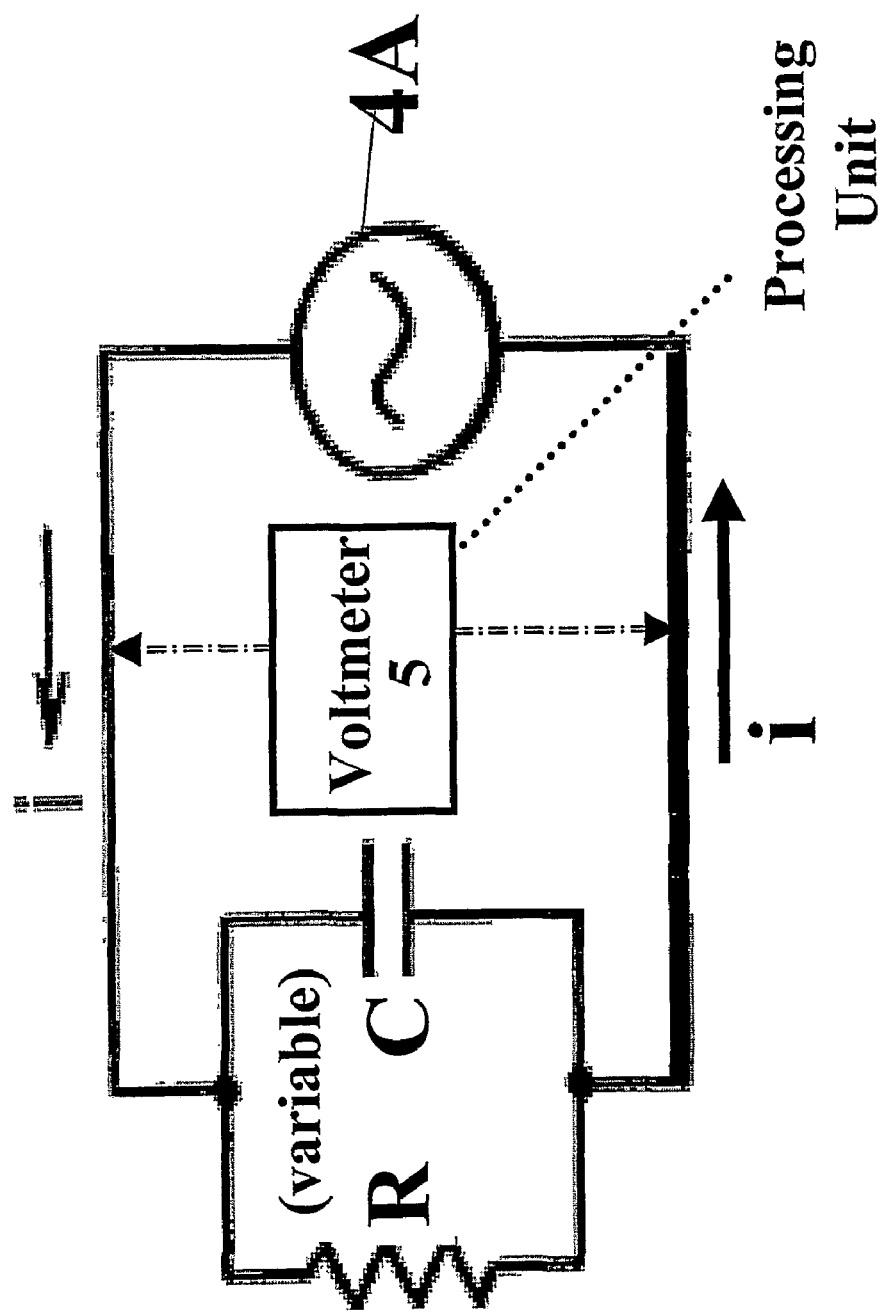

Not wishing to be bound by theory, it is noted that FIG. 2 provides an electrical model of the root canal region. Thus, according to FIG. 2, the region between the root canal electrode 2 (e.g. the tip 2A of the root canal electrode) and the external electrode 3 can be modeled as a resistor in parallel with the capacitor. The values of the resistance and the capacitance vary as a function of the distance between the root canal electrode and the apex of the tooth. Thus, the present inventors note that while the tip of the root canal electrode is in the dental neck or canal region 1A, the resistance component gradually decreases as the root canal electrode 2 intrudes deeper into the root canal 1. In the apex region 1B, the value of the resistance component typically reaches a value of about 6.5 K Ohm.

Once more, not wishing to be bound by theory, it is further noted that in contrast, the capacitive component, typically, is substantially constant while the tip 2A of the root canal electrode is in the dental neck or canal region 1B. The capacitive component typically increases abruptly when the tip of the root canal electrode reaches the apex region 1B.

According to these observations, the present inventors have noted that the resistive component of impedance is useful for determining the distance between a fixed point on the root canal electrode 2 and a fixed point in the apex region 1B when the tip of the root canal electrode is located in the dental neck region 1A. Furthermore, the capacitive component of impedance is useful when the tip of the root canal electrode is located in the apical region 1B.

In general, the relative weight of the resistive and capacitive components of impedance is determined, in part, by the values of the resistance and capacitance between the two electrodes. Furthermore, the relative weight of the resistive and capacitive components of impedance is also at least partially determined by the frequency of the measurement signals generated by the power source of measurement signal generator 4. Thus, certain embodiments of the present invention are motivated by the observation of the present inventors that a judicious choice of the measurement signal frequency (e.g. selection of a medium frequency) allows one to determine a distance between the fixed point on the root canal electrode and the fixed point in the apex region 1B (e.g. apical constriction, or tooth apex) by determining the value of a capacitance-governed function when the root canal electrode is in the apical region 1B. Furthermore, this same medium frequency also allows one determine a distance between the fixed point on the root canal electrode and the fixed point in the apex region 1B (e.g. apical constriction, or tooth apex) by determining the value of a function at least partially governed by resistance when the root canal electrode is in the dental neck region 1B. In some embodiments, "medium" frequencies, are between 50 KHZ and 300 KHZ. In some embodiments, "medium" frequencies, are between 50 KHZ and 200 KHZ. In some embodiments, "medium" frequencies, are between 50 KHZ and 250 KHZ.

As used herein, a "capacitance-governed function" is a function whose value is substantially independent of the value of resistance—e.g. a function whose value does not fluctuate substantially (e.g. does not change more than 5%, e.g. does not change more than 10%, e.g. does not change more than 20%) with fluctuations in resistance between the two electrodes due to changing the position of the root canal electrode in a certain region of the root canal (for example, in the apical region).

As used herein, a "resistance-governed function" is a function whose value does not fluctuate substantially (e.g. does not change more than 5%, e.g. does not change more than 10%, e.g. does not change more than 20%) with variations in capacitance due to changing the position of the root canal electrode. Typically, using a lower frequency (or direct current) will provide functions that do not fluctuate with variations in the capacitance.

As used herein, a "function at least moderately governed by resistance" is a function whose value does fluctuate (e.g. at least 15%, e.g. at least 30%) as values of the resistance changes (e.g. due to changing the positions of the root canal electrode). Thus, a "resistance-governed function" is one special case of a "function at least moderately governed by resistance."

According to some embodiments of the present invention, the current supply device or measurement signal generator 4 is operative to generate a time varying current (e.g. an alternating current) having a frequency of at least 50 KHZ. Furthermore, according to some embodiments of the present invention, the current supply device or measurement signal generator 4 is operative to generate a time varying current (e.g. an alternating current) having a frequency of at most 300 KHZ, or at most 200 KHZ.

It is noted that in the example provided, the device is a single frequency device, though this is not to be construed as a limitation of the present invention.

The following examples are brought for illustrative purposes only, and are not intended to limit the scope of the present invention.

Example 1

Experimental System

An evaluation system was built which provided a constant current of 10.8 microamperes at a frequency of 65 KHz between two electrodes.

The sensed voltage between the electrodes was digitized by an 8-bit analog digital converter (ADC), meaning that there were 255 possible signal levels. By appropriate scaling of the system (signal level and amplification, each level of the ADC represents 294 microvolt-RMS, between the electrodes). Since the current is 10.8 microamperes we get 27.33 Ohms per level.

The impedance/distance curve was measured at about 10 microamperes.

The measured level was digitally displayed.

The following look-up table was used to correlate between the measured impedance between the two electrodes and the distance between the tip of the root canal electrode and the apex of the tooth (the first column is in mm, The second column is in Ohms. For example: at 0.2 mm the impedance is 2.952 K Ohms.)

−0.1 2.405 E+3
0 2.651 E+3
0.1 2.815 E+3
0.2 2.952 E+3

0.3 3.088 E+3
0.4 3.252 E+3
0.5 3.416 E+3
0.75 3.799 E+3
1 4.072 E+3
1.5 4.373 E+3
2 4.591 E+3
2.5 4.783 E+3
3 4.947 E+3

Example 2

In Vitro Measurements

Extracted human teeth were inserted into a gum simulating mass (alginate). A dental file was pushed into the root canal of the measured extracted tooth. Measurements were taken at several depths of the file within the root canal.

To be able to measure the depth of the file the following procedure was used:

First, before putting the tooth into the alginate mass, the file was pushed into the extracted tooth until the file tip reached the apex. Then the distance between the file head and a reference point at the topside of the tooth was measured, yielding the zero reference point. Next, the tooth was inserted into the alginate mass and the measuring procedure began.

For each level, the voltage between the two electrodes was measured and translated into impedance.

The experiment was repeated several times per extracted tooth, and for several extracted teeth. Furthermore, as a control, the experiments were repeated using other apex locators systems—namely a "Morita Root ZX" and a "Dentsply ProPex."

Agreement was found between the measurements of the experimental system and the other locator systems—e.g. "Morita Root ZX" and a "Dentsply ProPex."

Mechanical measurements of the distance between the apex and the tip of the root canal electrode were also made. The position measurement in mm was done by using a calibrated digital micrometer down to 0.01 mm accuracy/resolution. Agreement was found between the mechanical measurements and those of the experimental system.

Example 3

Clinical Experiments

The clinical test prototype display of the experimental system showed directly the location as evaluated in the in-vitro tests.

We verified the reliability of the displayed values by using also the Root ZX and comparing the reached working length (final position in the vicinity of the apical constriction) with radiographs. (X-Ray images). Agreement was found by results of the experimental system and these other old systems.

Example 4

Exemplary System

Below is a specification of an exemplary systems in accordance with some embodiments of the present invention. Nothing in this example is intended as limiting. The entire example is intended only as illustrative. Furthermore, the skilled artisan will appreciate the certain elements in this Exemplary system are option, and other elements can be implemented in any number of ways.

Figure 3:
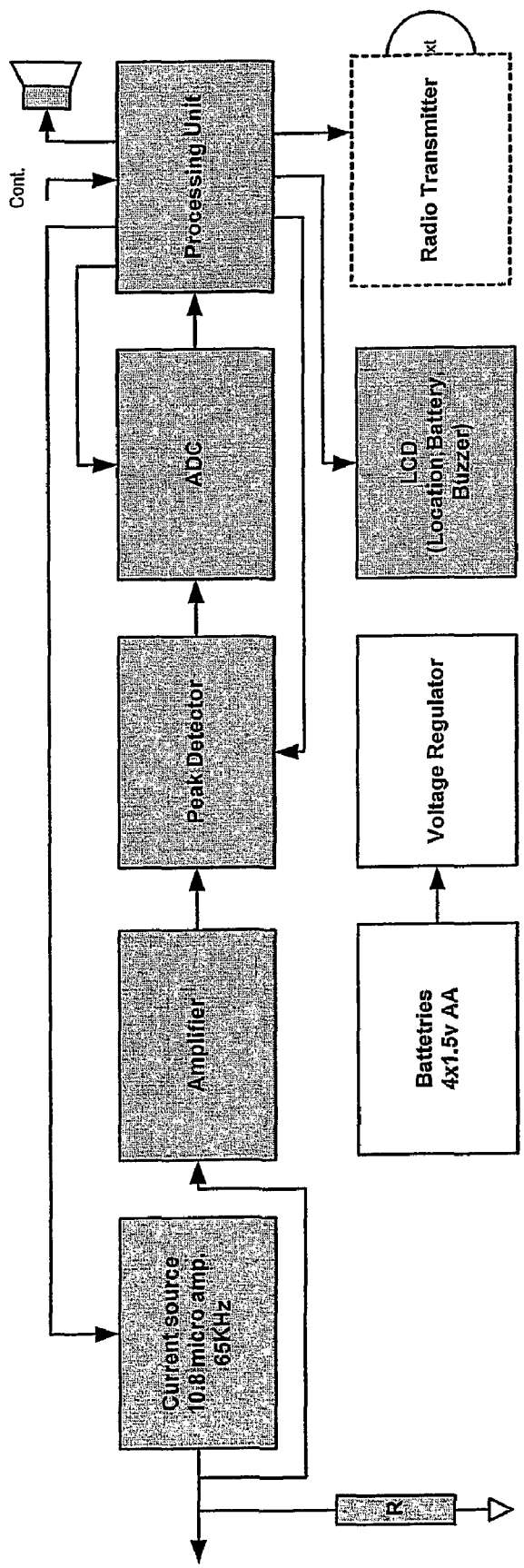

FIG. 3 is a block diagram of the exemplary system.

A current source generates a sinusoidal signal of 65 KHz or and feeds it into the tooth canal ("measured object").

Due to the constant current source and the very large resistance of the parallel resistor R the voltage on the measured object is relative to its impedance. Therefore, voltages on the measured object correspond to the impedances Z of the measured object.

Current Source

The signal current source provides 10.8 micro amps. At a frequency f=65 KHz and is controlled by the processing unit.

The current is injected into the load every 1 msec for a period of about 0.25 msec.

After an interruption of 0.75 msec, the frequency f is injected again and so forth periodically.

The peak value of the load current is protected to avoid exceeding 50 μA.

No DC current is allowed through the electrodes.

Amplifier

The amplifier stages are high input impedance stages with high common mode rejection as well as low frequency rejection.

Peak Detector

The peak detector is used for providing a measurement signal into the ADC and is reset every 1 msec. The reset is synchronized with the effective measurement signal.

ADC

The ADC converts the analog signal into a 256 level (8 bit) digital signal for evaluation by the processing unit.

The ADC is synchronized by the processing unit.

Controller/Processing Unit

Processing

The processing functions are:
1. Generation of the input modulation drive to the current source.
2. Collecting ADC data and comparing to a preprogrammed calibration table.
3. Calculating the distance between the file and the apex, using a built in lookup table.
4. Converting the calculated location to input values for the LCD.
5. Initiating buzzer signal according to the file location.

Control

The control functions are:
1. Management and synchronizing of the measurement process and the signal flow (Peak detector, ADC).
2. Interface between the processing unit and the display and controls.
3. Measuring the battery voltage and driving the battery indication at the display.
4. Operating an audible signal.
5. Control the man machine interface (MMI).
6. Generate the internal system clock.
7. Generate and activate self test functions (if applicable).

Radio Communication

In a wireless operation version, the display input data is transmitted via wireless radio link towards a compatible receiver which is connected via USB to the dental chair integrated monitor. Specially installed software will provide a replica of the LCD on the monitor. The graphic appearance on the external monitor is designed separately.

External Interface
Connectors
1. Electrodes' connector: Standard earpiece connector
Controls
1. On/off—Pushbutton, 1 sec pressing for on or off activation. The unit will automatically turn off after 20 minutes.
2. Buzzer volume control.
3. Display illumination control.
4. Apical constriction indication signal level.
Display
1. Indications:
    a. The length display is between −0.3 mm and +3.0 mm. The scale is logarithmic for the values 0.0 to 3.0 mm, and linear for the values 0.0 to −0.3 mm
    b. Continuous beep in the range between Apical Constriction and Apex.
    c. On/Off beep at APEX location: 0.0 mm.
    d. At the value of the Apical Constriction (nominally at 0.5 mm) a special indication is seen on the display. This indication is pre-settable by the user in the range of 0.5 mm to 1.0 mm.
2. Battery voltage, audible signal at low battery.
3. On/Off indication of switch (display indications are observable).
Measuring Probes
The measuring probes consist of a two wire flexible cable 5 ft long.
One end is terminated with an earphone connector. The other end is split into two wires of 1 ft length.
One wire is terminated with a hook shaped electrode and the other with a spring clip electrode to be connected to the file.
Both types of electrode are detachable and replaceable.
Both types of electrode are autoclavable.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. Apparatus for detecting an apical position depending on the change in the impedance between a first current supply electrode inserted into the root canal of a tooth of a patient and a second current supply electrode contacting a body surface of the patient, the apparatus comprising: a) a detection apparatus including a measurement signal generator adapted to produce a regulated current between the first and second current supply electrodes, said detection apparatus adapted to sense an impedance-related parameter between the first and second current supply electrodes; and b) a processing unit for deriving from said sensed parameter a multiple of a distance between a fixed point on the first current supply electrode and the apical position of the tooth, wherein said regulated current has an amplitude that is substantially independent of a distance between said fixed point and the apical position.

2. The apparatus of claim 1 wherein said regulated current has a substantially constant current amplitude.

3. The apparatus of claim 1 wherein said regulated current is a time varying current having a frequency of at least about 50 KHz.

4. The apparatus of claim 3 wherein said regulated current is a time varying current having a frequency of at least about 50 KHz and at most about 200 KHz.

5. The apparatus of claim 1 wherein said processing unit determines a capacitance-governed function when the first electrode is in the apical region, and said processing unit determines a function at least moderately governed by resistance when the electrode is in a dental neck region.

6. The apparatus of claim 1 wherein said processing unit determines a capacitance-governed function when the first electrode is in the apical region, and said processing unit determines a function moderately governed by resistance when the electrode is in a dental neck region.

7. The apparatus of claim 1 wherein said detection apparatus is adapted to sense the impedance-related parameter and said processing unit is configured to sense the distance multiple without relying on measurement signals at multiple frequencies.

8. The apparatus of claim 1 wherein said detection apparatus is adapted to produce the regulated current between the electrodes at a single frequency of at least about 50 KHz.

9. A device comprising: a) a dental file electrode insertable into the root canal of a tooth of a patient; b) an external electrode adapted to contact a body surface of the patient; and c) a detection apparatus including a measurement signal generator adapted to produce a regulated current between said dental file and external electrode, said detection apparatus adapted to sense an impedance related parameter to generate an output signal indicative of a distance between a fixed point on said dental file electrode and the apical position of the tooth, wherein said regulated current has an amplitude that is substantially independent of a distance between said fixed point and the apical position.

10. The device of claim 9 wherein said regulated current is a substantially constant amplitude current.

11. The apparatus of claim 9 wherein said detection apparatus is adapted to sense the distance-indicative impedance-related parameter without relying on measurement signals at multiple frequencies.

12. The apparatus of claim 9 wherein said detection apparatus is adapted to produce the regulated current between the electrodes at a single frequency of at least about 50 KHz.

13. The device of claim 9 further comprising: d) a processing unit for deriving from said output signal a multiple of a distance between said fixed point on said first electrode and said apical position of the tooth.

14. The device of claim 13 wherein said processing unit determines a capacitance-governed function when the first electrode is in the apical region, and said processing unit determines a function moderately governed by resistance when the electrode is in a dental neck region.

15. A method of measuring penetration in a root canal of a tooth of a patient comprising: a) inserting a first electrode into the root canal of a tooth; b) applying a second electrode to a body surface of the patient; c) supplying a regulated current between said first and second electrodes; and d) determining an impedance parameter between said first and second electrodes, said impedance parameter indicative of a distance between a fixed point on said first electrode and an apical position of said tooth, wherein said first electrode is inserted to a plurality of depths within said root canal, and an amplitude of said regulated current is substantially independent of said distance between said fixed point and said apical position.

16. The method of claim 15 wherein said determining of said distance-indicative parameter is carried out without relying on measurement signals at multiple frequencies.

17. The method of claim 15 wherein electrical current at only a single frequency of at least about 50 KHZ is supplied between said first and second electrodes.

18. The method of claim 15 wherein said second electrode is applied to said position within the oral cavity of the patient.

19. The method of claim 15 wherein said second electrode is applied to said position outside of the oral cavity of the patient.

20. The method of claim 15 wherein said regulated current is a time varying current, and a frequency of said time varying current is at most about 250 KHZ.

21. The method of claim 15 wherein said regulated current is a time varying current, and a frequency of said time varying current is at least about 50 KHZ.

22. The method of claim 15 wherein said determining includes determining a capacitance-determined impedance parameter when said fixed point is in an apical region of said root canal, and determining an impedance parameter whose value is at least moderately governed by resistance when said fixed point is in a dental neck region of said root canal.

23. The method of claim 15 further comprising: c) deriving from said determined impedance parameter a multiple of a distance between said fixed point on said first electrode and said apical position of the tooth.

24. The method of claim 23 wherein said deriving of said multiple of said distance includes deriving a capacitance-governed function when said fixed point is in an apical region of said root canal, and deriving a function at least moderately governed by resistance when said fixed point is in a dental neck region of said root canal.

25. A method of measuring penetration in a root canal of a tooth of a patient comprising: a) inserting a first electrode into the root canal of a tooth; b) applying a second electrode to a body surface of the patient; c) supplying a regulated current between said first and second electrodes; and d) determining an impedance parameter between said first and second electrodes, said impedance parameter indicative of a distance between a fixed point on said first electrode and an apical position of said tooth, wherein said determining includes determining a capacitance-determined impedance parameter when said fixed point is in an apical region of said root canal, and determining an impedance parameter whose value is at least moderately governed by resistance when said fixed point is in a dental neck region of said root canal.

26. The method of claim 25 wherein said determining of said distance-indicative parameter is carried out without relying on measurement signals at multiple frequencies.

* * * * *